(12) United States Patent
Ellis et al.

(10) Patent No.: US 6,274,598 B1
(45) Date of Patent: *Aug. 14, 2001

(54) METHODS FOR TREATING ANTIBIOTIC-RESISTANT INFECTIONS

(75) Inventors: William Y. Ellis, Laurel, MD (US); Calvin M. Kunin, Columbus, OH (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/395,210

(22) Filed: Sep. 14, 1999

Related U.S. Application Data

(63) Continuation-in-part of application No. 08/957,817, filed on Oct. 27, 1997, now Pat. No. 5,965,572.
(60) Provisional application No. 60/029,214, filed on Oct. 28, 1996.

(51) Int. Cl.⁷ .................................................. A61K 31/445
(52) U.S. Cl. ............................................................ 514/315
(58) Field of Search ................................................ 514/315

(56) References Cited

U.S. PATENT DOCUMENTS 3,764,604 * 10/1973 Ash et al. ........................... 260/293.5
5,965,572 * 10/1999 Ellis et al. ............................ 514/311

* cited by examiner

*Primary Examiner*—Kevin E. Weddington
(74) *Attorney, Agent, or Firm*—Elizabeth Arwine; Charles H. Harris

(57) ABSTRACT

This invention relates to the treatment of antibiotic-resistant infections, including particularly infections caused by bacteria, Mycobacteria and fungi. A preferred group of compositions of the invention contain as active agents compounds containing pyridyl, quinolyl or benzoquinolyl ring systems substituted on the nitrogen-containing ring at the carbon opposite the nitrogen by a carbon bound to an oxygen which is also bound to a nitrogen through a saturated carbon or carbon chain, or, in the case of the pyridyl ring system, the substituent at the 4 position of the pyridyl ring may be an alkyl which may be substituted with halo, hydroxy, alkoxy, amino or alkylamino.

11 Claims, No Drawings

METHODS FOR TREATING ANTIBIOTIC-RESISTANT INFECTIONS

This application is a continuation-in-part of U.S. patent application Ser. No. 08/957,817, filed Oct. 27, 1997, now U.S. Pat. No. 5,965,572 which claims priority from Provisional Patent application No. 60/029,214, filed Oct. 28, 1996.

FIELD OF THE INVENTION

This invention relates to the treatment of antibiotic-resistant infections, including particularly infections caused by bacteria, Mycobacteria and fungi. A preferred group of compositions of the invention contain as active agents compounds containing pyridyl, quinolyl or benzoquinolyl ring systems substituted on the nitrogen-containing ring at the carbon oposite the nitrogen by a carbon bound to an oxygen which is also bound to a nitrogen through a saturated carbon or carbon chain, or, in the case of the pyridyl ring system, the substituent at the 4 position of the pyridyl ring may be an alkyl which may be substituted with halo, hydroxy, alkoxy, amino or alkylamino.

BACKGROUND OF THE INVENTION

The benefit from use of antibiotics as a means of treating infections has been increasingly compromised by the development of resistant strains of microorganisms. Most of the new drugs are derivatives of older compounds. It is necessary to develop new agents that will respond to the current needs for medicinals that will effectively control pathogenic microbial populations that are resistant to antibiotics.

Mefloquine is quinolyl compound having two trifluoromethyl groups attached to the quinolyl ring. This compound has been used to treat malaria. It has also been found to have some activity against bacterial pathogens in vitro.

SUMMARY OF THE INVENTION

This invention comprises compositions containing as active agents compounds which have pyridyl or quinolyl ring systems (including benzoquinolyl ring systems) substituted at the carbon opposite the nitrogen by a carbon bound directly to an oxygen and to a nitrogen through a saturated carbon or carbon chain or, in the case of pyridyl, an alkyl, alkenyl, alkyloxy, alkenyloxy, amino or alkylamino group wherein alkyl has 1–6 carbons, alkenyl has 2–6 carbons, wherein said alkyl or alkenyl groups may, optionally, have amino, hydroxy or halo substituents. Preferred compounds of the invention are those wherein the quinolyl ring system has at least one electron-rich substituent on the quinolyl ring system, including, for example, halo, phenyl, hydroxy, alkoxy or trihalomethyl substituents and the substituent at the carbon directly opposite the nitrogen atom is of the structure —CHOYX wherein Y may be a second bond to the oxygen or may be carboxyl, ether or ester moiety wherein the ether or ester moiety may be alkyl of 1–8 carbons, phenyl, phenylalkyl wherein the alkyl moiety consists of 1–4 carbons and wherein any said alkyl or phenyl group may, additionally, be substituted with hydroxy, alkyl of 1–2 carbons, alkenyl of 2–3 carbons, halo, amino, or alkyl amino group, X is $CH_2N((CH2)_n(CH_3)_m$ wherein n is $\leq 5$, m is 1 or 2 with the proviso that when m is 2, n is $\leq 3$, or X may be $CH_2N(CH_2)_q$ wherein q may be up to 10, which is cyclized and may have up to 4 bridge carbons or X is a saturated six-member nitrogen containing ring which may be substituted, wherein the piperidinyl moiety is bound through the carbon at the 2 position of the ring to the CHOY through a carbon atom. The six member ring may have 1–4 bridge carbons to produce complex ring systems such as quinuclidinyl ring systems.

The active agents are useful for treating patients suffering from infections including gram positive bacteria, gram negative bacteria, fungi and mycobacteria. They are effective against strains which have shown resistance to other antimicrobial agents.

DETAILED DESCRIPTION OF THE INVENTION

It has been found that compositions of the following formula:

wherein N is a quinolyl, pyridyl or benzoquinolyl ring substituted at the carbon opposite the nitrogen on the nitrogen-containing ring by B—A wherein B is a carbon (C') bound to an oxygen, (=O, OH, Oalk, OCOalk, OCOaryl, OCOphenyl alkyl, or an oxygen in a cyclic moiety wherein aryl is phenyl or naphthyl and alkyl has 1–4 carbons and may be substituted hydroxy, or with 1–2 halo atoms) and wherein said carbon C' is also bound A, which is a saturated carbon which is bond directly to a nitrogen-containing saturated chain or nitrogen-containing saturated ring system (for example, piperidinyl or quinuclidinyl ring systems), wherein any saturated ring system may be substituted with alkyl, alkenyl, halo, alkoxy or haloalkyl moieties of 1–5 carbons or with phenyl, phenoxy, phenylalkyl, phenylalkoxy, carboxy or carbonyl groups, wherein the carboxy or carbonyl groups, including keto or ester moieties with alkyl groups of 1–4 carbons, alkenyl groups of 2–5 carbons or phenylalkyl wherein the alkyl is of 1–3 carbons. Z is $R_{1(m)}$ and/or $R_{2(n)}$ wherein at least one of $R_1$ and $R_2$ is an electron-rich substituent and m and n may be 1–4 and wherein $R_1$ and/or $R_2$ may be alkyl, alkoxy, aryl, aryloxy, aryloxyalkyl, amino, aminoalkyl, alkylaminoalkyl, arylamino, alkenyl, arylalkenyl, arylalkylaminoalkyl, carboxyalkyl, hydroxy, halo, alkenyl, alkenyloxy, herein any alkyl has 1–8 carbons, alkenyl has 2–8 carbons, halo is chloro, fluoro or bromo and aryl is a ring system of 1–3 rings. Preferred electron-rich substituents are chosen from moieties containing unsaturated ring systems (such as phenyl, phenoxy and naphthyl), halo (preferably chloro, fluoro) trihalomethyl, alkoxy, alkenyloxy, alkylamino and aminoalkylamino groups wherein any alkyl has 1–8 carbons. However, when N is quinolyl, if the 2 position on the quinolyl ring is substituted with trihalomethyl and the 8 position is substituted with trihalomethyl or phenyl, the 6 or 7 position on the ring system must be further substituted with an electron-rich substituent such as halo or alkoxy. The preferred compounds of the invention require specifically a large substituent such as phenyl, phenoxy, naphthyl, trihalomethyl (particularly trifluoromethyl) or quinuclidinyl groups at the 2 position on the ring system. Any alkyl or aryl moiety may further be substituted with halo, hydroxy, amino, alkylamino, alkylamino groups having 1–4 carbons or alkenyl, alkenylamino of 2–4 carbons.

When N is a pyridyl ring, the 2 and 6 positions of the pyridyl ring must be substituted with aryl groups wherein aryl is phenyl or naphthyl. Compounds may be made by usual means. The following schemes are appropriate:

3
4
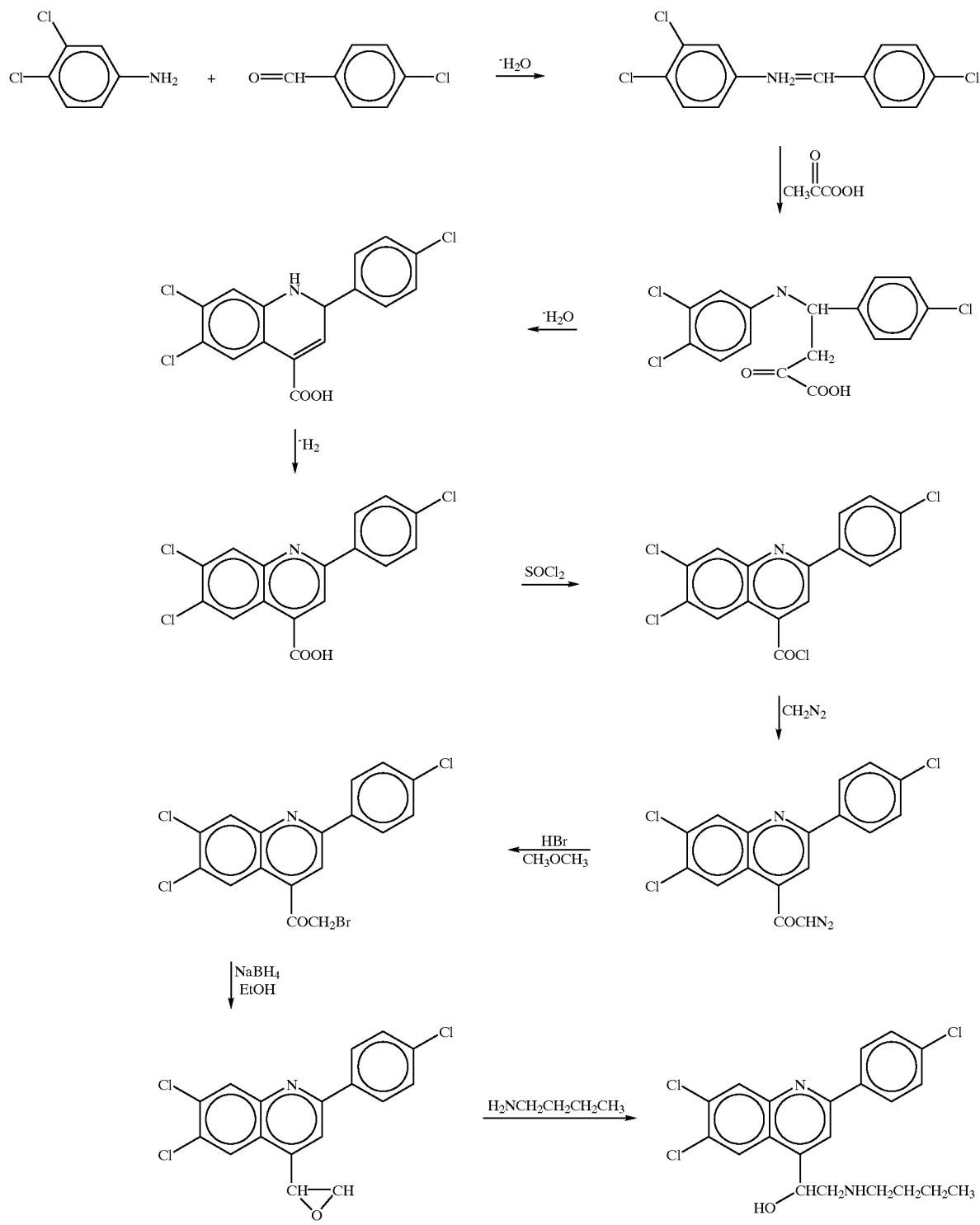
Cinchoninic Acid by Doebner Reaction
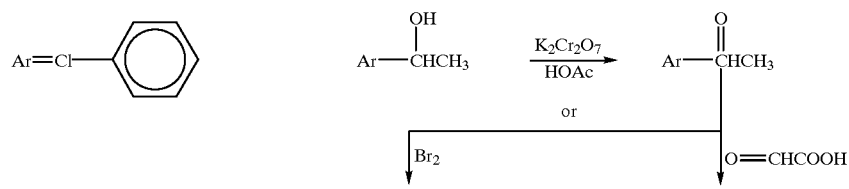

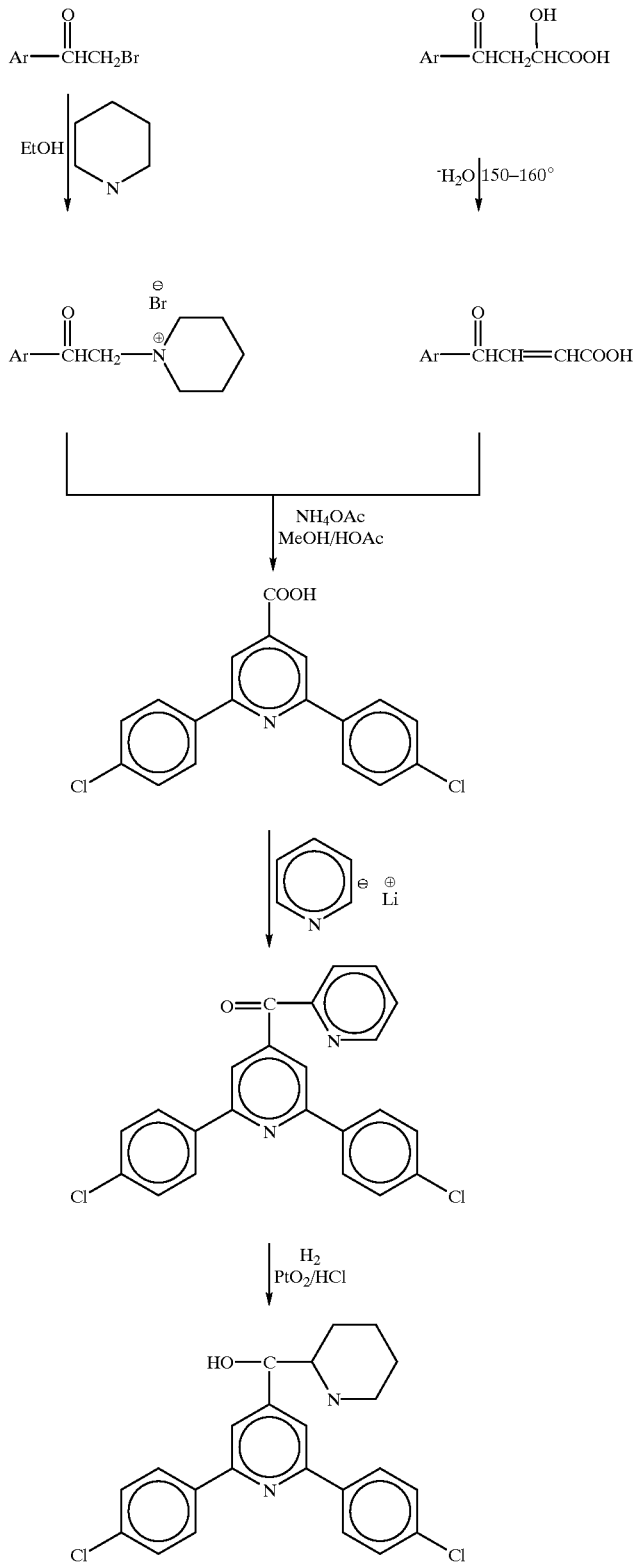

Particularly preferred compounds are of the formula:

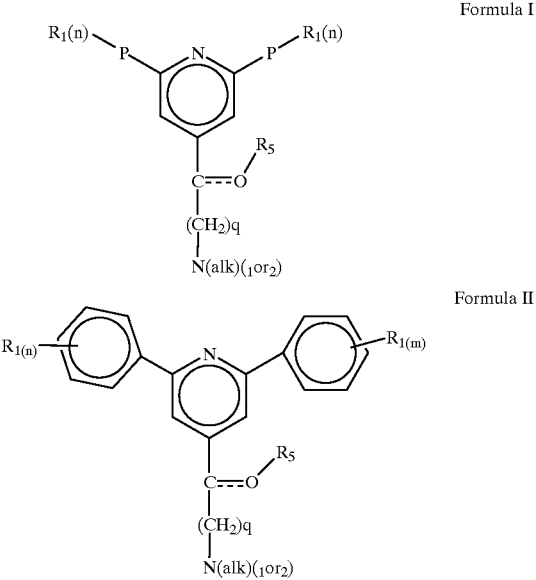

Formula I

Formula II wherein P is phenyl or napthyl, q is 1–3, and, in N(alkyl)$_{(1 \text{ or } 2)}$, alkyl is of 1–8 carbons which may be substituted with halo or alkoxy and $R_5$ is H or alkyl of 1–4 carbons and, in formula II, wherein at least 1 of $R_1$ or $R_2$ is halo, haloalkyl, dihaloaklyl, trihaloalkyl or alkoxy, or compounds of the formula:

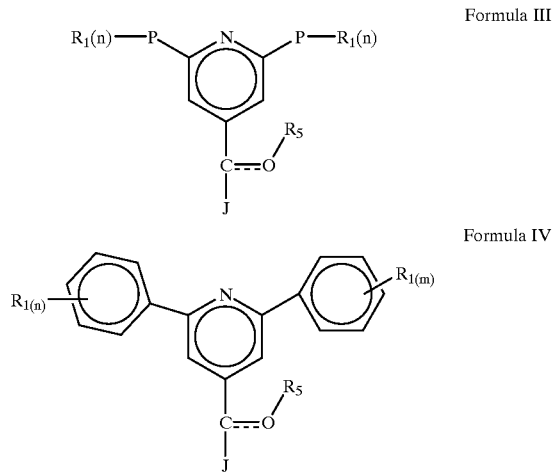

Formula III

Formula IV wherein P is phenyl or napthyl, $R_5$ is H or alkoxy, J is a saturated nitrogen containing ring attached at the 2 position of ring J which may be substituted with halo or alkoxy and, in Formula IV, at least 1 of $R_1$ is halo, haloalkyl, dihaloaklyl, trihaloalkyl or alkoxy.

In compounds of formula I and II, the N-dialkyl compounds are active against mycobacteria, but not against gram negative organisms or bacteria. Hence, for broad spectrum activity, compounds of wherein, for N(alkyl) ($_1$ or $_2$) mono subsitution ($_{(1)}$) are preferred.

Materials and Methods

Active agents of the invention were tested for activity against several infectious organisms. Testing for inhibitory effect against antibiotic-resistant organisms was accomplished in the following manner:

Media

The strains were streaked on blood agar plates (trypticase soy broth containing 5% sheep cells). A single colony was isolated and grown in Mueller-Hinton Broth (MHB) as recommended by the national Committee for Clinical Laboratory Standards for rapidly growing bacteria. Candida species and related fungi were isolated in a similar manner on brain-heart infusion agar (BHI).

Susceptibility Tests

The antibiotic susceptibility profile of each strain was determined using standard microtiter dilution plates obtained from the Clinical Microbiology Laboratory at Ohio State University Hospitals. The Inocula were prepared by suspending a 4 hour log phase growth in MHB visually equal in turbidity of an 0.5 McFarland standard. Inocula were further diluted and added to microdilution trays to achieve a final density of approximately $1 \times ^{-}10^5$ CFU/ml. The trays were incubated for 16 to 20 hours at 35° C. The highest dilution at which wells remained clear was considered to be the minimum inhibitory concentration (MIC).

The MIC and minimum bacterial concentration (MBC) of the strains to the active agents were determined by two-fold dilutions in Mueller-Hinton broth. Susceptibility tests for ATCC-obtained microorganisms and clincal isolates of gram positive bacteria including methicillin-susceptible and resistant Staphylococci, Streptococci, Pneumococci and gram negative bacteria, including Enterobacteriaceae, Pseudomonas, Hemophilus and Neisseria, were performed in microtiter plates as described above. The MIC and MBC were determined after 48 hours incubation at 35–37° C. A sample of 0.01 ml was taken from each clear well at the MIC end-point and streaked on trypticase soy agar plates. After 24 hours incubation, the number of colonies was counted. The amount of the agent required to kill 99.9% of the bacteria was determined as the MBC. Susceptibility tests for ATCC isolates of Candida and other fungi were performed in BHI broth according to the NCCLS method. Two ml of MHB containing serial dilutions of the agents compounds were added to 13×100 mm tubes. An inoculum of 0.1 ml (prepared as described above) was then added to each tube. The final inoculum was approximately $1 \times 10^{-3}$ to $1 \times 10^{-5}$ CFU/ml. The tubes were incubated at 35° C. in ambient air and read at 24 hours. The highest dilution at which the tubes remained clear was considered to be the MIC.

The MBC was determined as follows: After 48 hours incubation, tubes without visible growth were vortexed. A sample of 0.01 ml was taken from each tube and streaked on trypticase soy agar plates. After 24 hours, incubation, the number of colonies was counted. The amount of agent required to kill 99.9% of bacterial inoculum in the inoculum was determined as the MBC. Susceptibility tests for Mycobacteria were performed according to standard methods at the national Institutes of Health.

Compounds of the invention were dissolved in 1 ml of methanol and stored in aliquots at −70° C. They were diluted in Mueller-Hinton broth for final screening. Compositions were tested in 0.1 ml volumes by serial dilution in microtiter plates against *Staphylococcus aureus* methicillin-sensitive ATCC 29213 and the methicillin-resistant wild type T67738, as described above. The T67738 was resistant to most antimicrobial drugs, including ciprofloxacin.

The most active compounds were studied further by time and dose-related killing curve analysis using large inocula ($1 \times 10^7$ CFU/ml).

The lipid solubility of these compounds should permit the drugs to enter into cells and the central nervous system. The compounds would also be absorbed orally.

The dosage and method of administration will depend on the location of the infection, the condition of the patient and the availability of professional supervision. Methods of administration include parenteral, oral, buccal, nasal or endotracheal routes. The active agents may be administered as sprays. For nasal administration, the active agent may be delivered as a powder that is snorted. Inclusion complexes such as cyclodextrin inclusion complexes are appropriate compositions and would be particularly useful for buccal administration of these active agents.

The compounds of the invention may also be administered topically by any means, including by rectal route. Suppositories, solutions for use as retention enemas, and creams or jellies are appropriate carriers for use in rectal administration.

Compounds of the invention may be applied to the skin or mucosa, including the vaginal mucosa, using creams, jellies, suppositories, or solutions. The active agents of the invention may be delivered directly to the epithelial tissue topically. During surgery example of such use could involve the application of compositions containing the active agents of the invention to the exposed tissue and prosthetic devices. The compositions could be given by aerosol into the trachea or administered in mist along with other agents used in respiration therapy.

The compositions of the invention may also be used prophylactically to protect from infection by pathogenic organisms.

Dosage forms containing 25 to 1000 mg for administration by mouth are appropriate.

The concentration required to provide benefit was studied. The results may be seen in Table I

TABLE I

Active Agent:

| | | | | Effective Concentration ($\mu$g/ml) S. aureous | | |
|---|---|---|---|---|---|---|
| N | B | A | Z | Sens. | Resist. | Mycobacteria |
| quin* (#5801) | C=O | $(CH_2)_4CHCH_3NH_2$ | 2 phenyl, 7 Cl | | 6.25 | |
| quin (#6006, HCl salt) | CHOH | piperidinyl$^{(i)}$ | 2 phenyl, 8 Cl | 3.13 | 6.25 | |
| quin (#7555, phosphate) | CHOH | piperidinyl | 2 $C_4H_9HN$ | 6.25 | 6.25 | |
| quin (#7929) | CHOH | piperidinyl | 2 (4 Cl phenyl) | 6.25 | 6.25 | |
| quin (#7930) | CHOH | piperidinyl | 2 phenyl, 6,8 Cl | <.08 | 1.6 | 2 |
| quin (#7936) | CHOH | piperidinyl | 2 (4 chlorphenyl) 6,8 dichloro | <0.8 | <0.8 | |
| quin (#7939) | CHOH | piperidinyl | 2 phenylethenyl | 3.13 | 6.25 | |
| quin | $CHOSi(CH_3)_3$ | piperidinyl | 2 phenylethenyl | 3.13 | 6.25 | |
| quin (#117110) | CHOH | piperidinyl | 2 (4 clorophenyl)amino 6,8 dimethyl | <0.8 | <0.8 | |
| quin (#148987) | CHOH | piperidinyl | 2 (4 chlorophenoxy) 6 chloro | 3.13 | 6.25 | |
| quin (#159314, HCl salt) | CHOH | piperidinyl | 2,8 $CF_3$, 6 methoxy | 6.25 | 3.13 | |
| quin (#166391) | CHOH | piperidinyl | 2 quinuclidinyl 6,8 dichloro | <0.8 | <0.8 | 1 |
| quin (#169446) | C=O | piperidinyl | 2 phenyl 6,8 dichloro | 1.6 | 1.6 | 2 |
| quin (#211923, HCl salt) | CHOH | piperidinyl | 2(4-phenylphenyl) | <0.8 | <0.8 | 2 |
| quin (#259398) | CHOH | piperidinyl | 2(3,4-dichlorophenyl) 6 methoxy | 1.56 | 1.56 | |
| quin (#112312, oxide) | CHOH | 3 ethyl-quinuclidinyl | 6 methoxy | 1.56 | 1.56 | 128 |
| benzoquin** (#7333) | CHOH | piperidinyl | 2 phenyl | 1.56 | 1.56 | |
| benzoquin (#7573) | CHOH | piperidinyl | 2 (4 Cl-phenyl) | 0.8 | 0.8 | 0.5 |
| benzoquin (#94413) | CHOH | piperidinyl | 7,8 dimethoxy | 1.56 | 1.56 | |
| benzoquin (#100305) | CHOH | piperidinyl | 2 $CF_3$ | | 3.0 | |
| pyridyl (#142072) | CHOH | $CH_2N(C_2H_5)_2$ | 2,6 di(4-Cl-phenyl) | | 3.0 | |
| pyridyl (#144809) | CHOH | piperidinyl | 2,6 di(4-Cl-phenyl) | 1.56 | 1.56 | 0.5 |
| pyridyl (#148757, | CHOH | quinuclidinyl | 2,6 di(4-Cl-phenyl) | 1.5 | | 0.5 |

TABLE I-continued

Active Agent:

| N | B | A | Z | Effective Concentration (μg/ml) S. aureous Sens. | Resist. | Mycobacteria |
|---|---|---|---|---|---|---|
| HCl salt) pyridyl (#150089) | CHOH | CH$_2$N(CH$_3$)$_2$ | 2,6 di(4-Cl-phenyl) | | 3.0 | |
| pyridyl (#151312, HCl salt) | CHOH | CH$_2$N(CH$_4$H$_9$) | 2,6 di(4-CF$_3$-phenyl) | | 1.56 | |
| pyridyl (#153133, HCl salt) | CHOH | CH$_2$N(CH$_3$) (C$_4$H$_9$) | 2,6 di(4-Cl-phenyl) | | 3.0 | |
| pyridyl (#153136, HCl salt) | CHOH | CH$_2$NHCH(C$_3$H$_7$)$_2$ | 2,6 di(4-Cl-phenyl) | | 3.0 | |
| pyridyl (#153141, HCl salt) | CHOH | piperidinyl | 2,6 di(4-CF$_3$-phenyl) | | 1.5/3.0 | 0.5 |
| pyridyl (#158483, HCl salt) | CHOH | CH$_2$NHC$_5$H$_{11}$ | 2,6 di(4-CF$_3$-phenyl) | | 6.2 | |
| pyridyl (#171874, HCl salt) | CHOH | CH$_2$NHCH(CH$_2$H$_5$) (CH$_3$) | 2,6 di(4-CF$_3$-phenyl) | | 3.0 | |
| pyridyl (#171878, HCl salt) | CHOH | CH$_2$NH(CH$_2$H$_5$) | 2,6 di(4-CF$_3$-phenyl) | | 3.0 | |
| pyridyl (#172938, HCl salt) | CHOH | CH$_2$NH(CH$_3$H$_7$) | 2,6 di(4-CF$_3$-phenyl) | | 3.0 | |
| pyridyl | CHOH | CH$_2$NH(CH$_4$H$_9$) | 2-(4-Cl-phenyl), 6 naphthyl | | 3.0 | |
| pyridyl (#144809) | CHOH | Piperidinyl | 2,6 di(4-Cl-phenyl) | | | |
| Quinolyl (#7387) | CHOH | piperidinyl | 2 (4 methyl phenyl) 8 methyl | | | |

*quinolinyl
(i)the piperidinyl is bound to the carbon CHOH at the 2 position unless stated otherwise
**Benzoquinoline
144809 is effective against *Cyclosporidium parvum* at a concentration of 10 μg/ml with 79.3% inhibition
7387 is effective against Cylcoporidium at the same concentration with 71.2 inhibition
Both show a toxicity of 1 on a scale of 1 → 4 where 4 is unacceptable

EXAMPLE 1

Capsules of a formulation of active agent designated #112312 for oral administration are prepared by containing 250 mg. of the active agent, 100 mg. starch, and 5 mg. magnesium stearate. The capsules are administered daily or twice a day to achieve a daily dosage of 500 mg. per day.

EXAMPLE 2

A preparation for application to the skin or mucosa may be prepared in the following manner:

| Ingredient | % w/w |
|---|---|
| Compound #166391 | 15.0% |
| glyceryl monostearate | 3.0% |
| Petrolatum | 83.5% |

EXAMPLE 3

A formulation for administration as a retention enema may be formulated in the following manner:

| Ingredient | w/w % |
|---|---|
| Compound #211923 | 15% |
| Propylene glycol | 85% |

When the active agent is administered to the mucosa of the oral cavity, it may be administered as a buccal tablet or spray for use in the oral-pharyngeal cavity and the nasal cavities.

EXAMPLE 4

To 15 ml of phosphate buffered saline is added 3 mg of compound #7573. The composition is placed in a bottle having a stopper with a smooth glass rod extending into the solution. The composition is applied to boils using the smooth glass rod as an applicator. The composition may also be administered as a spray from a bottle with an atomizer.

EXAMPLE 5

To a 4×4 inch bandage having a smooth surface on one side there is applied to the smooth surface 0.02 ml of the solution prepared as a 2 μM solution of active agent designated # 7936 in PBS. The prepared bandage is then enclosed in a foil covering which is made air-tight. For application, the bandage is unwrapped and is applied smooth side down on the wound.

EXAMPLE 6

A composition is prepared for use on the skin or mucosa in the following manner:

| Ingredient | % w/w |
|---|---|
| Agent desiganted #144809 | 0.5% |
| propylene glycol | 13.0% |
| Phosphate buffered saline | 86.5% |

When the active agent is administered to the mucosa of the oral cavity, it may be administered as a buccal tablet or spray for use in the oral-pharyngeal cavity and the nasal cavities.

EXAMPLE 7

A composition prepared as a gel for application to the skin:

| Ingredient | % w/w |
|---|---|
| active agent designated #148757 | 0.5% |
| propylene glycol | 10.0% |
| Polyethylene glycol | 89.5% |

EXAMPLE 8

A composition prepared for administration as a suppository:

| Ingredient | % w/w |
|---|---|
| active agent #153141 | 0.5 mg |
| glyceryl monosterate | 1.0 Gm |
| hydrogenated coconut oil | 1.0 Gm |
| glyceryl monopalmitate | 1.0 Gm |

Compounds of the following structure showed particularly high activity:

What is claimed is:

1. A method of treating a patient suffering from infection caused by bacteria, mycobacteria or fungi by administration to said patient of a composition containing as an active agent bacteria, mycobacterium or yeast growth-inhibiting effective amount of a compound of the formula:

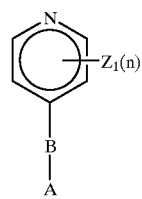

wherein B is a carbon (C') bound to an oxygen, (=O, OH, Oalk, OCOalk, OCOaryl, OCOphenyl alkyl, or an oxygen in a cyclic moiety wherein aryl is phenyl or naphthyl and alkyl has 1–4 carbons and may be substituted hydroxy, or with 1–2 halo atoms, said moeities being defined as A) and wherein said carbon C' is also bound to a saturated carbon which is bond directly to a nitrogen-containing saturated chain or nitrogen-containing saturated ring system (for example, piperidinyl or quinuclidinyl ring systems), wherein any saturated ring system may be substituted with alkyl, alkenyl, halo, alkoxy or haloalkyl moieties of 1–5 carbons or with phenyl, phenoxy, phenylalkyl, phenylalkoxy, carboxy or carbonyl groups, wherein the carboxy or carbonyl groups, including keto or ester moieties with alkyl groups of 1–4 carbons, alkenyl groups of 2–5 carbons or phenylalkyl wherein the alkyl is of 1–3 carbons or wherein Z is $R_1$ and/or $R_2$ wherein at least one of $R_1$ and $R_2$ is an electron-rich substituent and n may be 1–4 and wherein $R_1$ and/or $R_2$ may be alkyl, alkoxy, aryl, aryloxy, aryloxyalkyl, amino, amino-alkyl, alkyl-aminoalkyl, arylamino, alkenyl, arylalkenyl, arylalkylaminoalkyl, carboxyalkyl, hydroxy, halo, alkenyl, alkenyloxy, herein any alkyl has 1–8 carbons, alkenyl has 2–8 carbons, wherein halo is chloro, fluoro or bromo and aryl is a ring system of 1–3 rings which may be substituted by halo, alkyl, alkoxy, alkenyl, alkenyloxy, wherein any alkyl may be substituted with halo, amino or alkoxy.

2. A method of claim 1 wherein said active agent is of the formula:

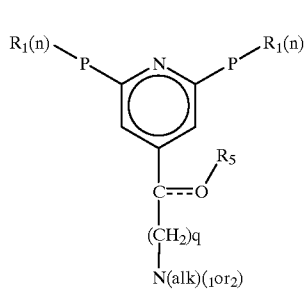

Formula I

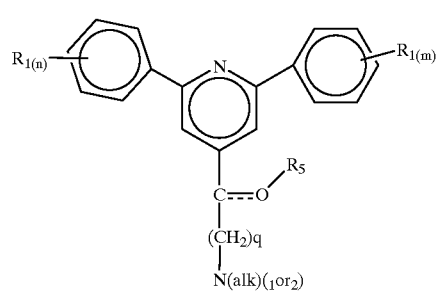

Formula II wherein P is phenyl or naphthyl, q is 1–3, and, in $N(alkyl)_{(1\ or\ 2)}$, alkyl is of 1–8 carbons which may be substituted with halo or alkoxy and $R_5$ is H or alkyl of 1–4 carbons, n and m are any of 1, 2, 3 or 4, and, in formula II, wherein at least 1 of $R_1$ or $R_2$ is halo, haloalkyl, dihaloaklyl, trihaloalkyl or alkoxy.

3. A method of claim 1 wherein said active agent is of the formula:

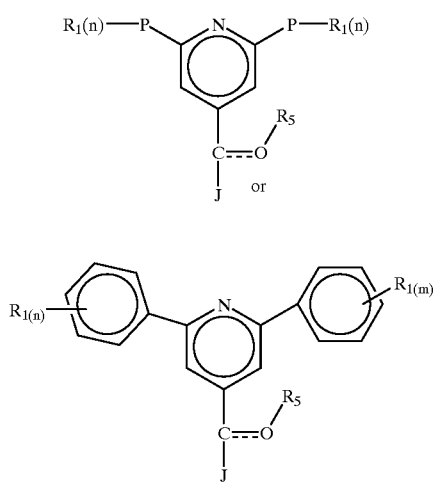

wherein P is phenyl or naphthyl, $R_5$ is H or alkoxy, J is a saturated nitrogen containing ring attached at the 2 position of ring J which may be substituted with halo or alkoxy, n and m are each 1, 2, 3, or 4, and, in Formula IV, at least 1 of $R_1$ is halo, haloalkyl, dihaloaklyl, trihaloalkyl or alkoxy.

4. A method of claim 2 having the substituent N $(alk)_1$.

5. A method of claim 1 wherein the active agent is at least one compound chosen from those wherein:

| B | A | Z |
|---|---|---|
| CHOH | $CH_2N(C_2H_5)_2$ | 2,6 di(4-Cl-phenyl) (#142072) |
| CHOH | piperidinyl | 2,6 di(4-Cl-phenyl) (#144809) |
| CHOH | quinuclidinyl | 2,6 di(4-Cl-phenyl) (#148757, HCl salt) |
| CHOH | $CH_2N(CH_3)2$ | 2,6 di(4-Cl-phenyl) (#150089) |
| CHOH | $CH_2N(CH_4H_9)$ | 2,6 di(4-$CF_3$-phenyl) (#151312, HCl salt) |
| CHOH | $CH_2N(CH_3)(C_4H_9)$ | 2,6 di(4-Cl-phenyl) (#153133, HCl salt) |
| CHOH | $CH_2NHCH(C_3H_7)_2$ | 2,6 di(4-Cl-phenyl) (#153136, HCl salt) |
| CHOH | piperidinyl | 2,6 di(4-$CF_3$-phenyl) (#153141, HCl salt) |
| CHOH | $CH_2NHC_5H_{11}$ | 2,6 di(4-$CF_3$-phenyl) (#158483, HCl salt) |
| CHOH | $CH_2NHCH(CH_2H_5)(CH_3)$ | 2,6 di(4-$CF_3$-phenyl) (#171874, HCl salt) |
| CHOH | $CH_2NH(CH_2H_5)$ | 2,6 di(4-$CF_3$-phenyl) (#171878, HCl salt) |
| CHOH | $CH_2NH(CH_3H_7)$ | 2,6 di(4-$CF_3$-phenyl) (#172938, HCl salt) |
| CHOH | $CH_2NH(CH_4H_9)$ | 2-(4-Cl-phenyl),6 naphthyl. |

6. A method of claim 1 wherein the composition is administered orally.

7. A method of the invention wherein the composition is administered to the mucosa.

8. A method of the invention wherein the composition is administered parenterally.

9. A method of claim 1 wherein the composition is administered intravenously.

10. A method of claim 1 wherein the composition is nasally or endotracheally.

11. A method of claim 1 wherein the composition is administered as a spray.

* * * * *